United States Patent [19]

Gilmore et al.

[11] 4,366,713

[45] Jan. 4, 1983

[54] ULTRASONIC BOND TESTING OF SEMICONDUCTOR DEVICES

[75] Inventors: Robert S. Gilmore, Burnt Hills; Homer H. Glascock, II; Harold F. Webster, both of Scotia, all of N.Y.

[73] Assignee: General Electric Company, Schenectady, N.Y.

[21] Appl. No.: 247,199

[22] Filed: Mar. 25, 1981

[51] Int. Cl.³ .......................................... G01N 29/04
[52] U.S. Cl. ........................................ 73/618; 73/588
[58] Field of Search ............... 73/618, 620, 624, 582, 73/588, 600

[56] References Cited

U.S. PATENT DOCUMENTS

| | | | |
|---|---|---|---|
| 3,295,089 | 12/1966 | Moore | 338/204 |
| 3,584,327 | 6/1971 | Murray | 15/104.16 |
| 4,008,602 | 2/1977 | Love | 73/609 |
| 4,011,748 | 3/1977 | Bond et al. | 73/618 |
| 4,252,263 | 2/1981 | Houston | 228/193 |

OTHER PUBLICATIONS

Wang et al., 1977 Ultrasonics Symposium Proceedings, IEEE Cat. No. 77CH1264-1SU, pp. 171-175.
Gilmore et al., Materials Evaluation, vol. 37, No. 1, Jan. 1979, pp. 65-72.

Primary Examiner—Stephen A. Kreitman
Attorney, Agent, or Firm—Donald R. Campbell; James C. Davis, Jr.; Marvin Snyder

[57] ABSTRACT

The bond between a structured copper heat sink member and a semiconductor wafer is inspected for voids and unbonds by a focused ultrasonic pulse transmission method. The small focused spot of ultrasound is transmitted along the structured copper strands and is attenuated in the lateral direction. The absence of a received pulse or a significantly reduced amplitude signal, as the assembled device is scanned with acoustic pulses, indicate flaws in the bond.

10 Claims, 6 Drawing Figures

ULTRASONIC BOND TESTING OF SEMICONDUCTOR DEVICES

BACKGROUND OF THE INVENTION

This invention relates to an ultrasonic pulse transmission method of detecting and mapping unbonded areas in a semiconductor device-to-structured copper bond.

In order to minimize electrical resistance heating and to maximize the conduction of heat away from the semiconducting layers, it is necessary that the interface of the semiconductor and heat sink be free from voids and unbonds. Since all bonding techniques such as soldering, brazing, diffusion, and thermal compression bonding can produce unattached areas and voids, it is necessary to detect the presence of such flaws and to determine their size, in order to make a proper quality assurance decision. The use of X-rays is not effective because the unbonded area usually does not result in a sufficient change in section thickness to be detected, even by computerized tomography. High frequency pulse-echo ultrasonic evaluations of phase inversions have proven to be an effective test of the semiconductor bond to tungsten and molybdenum heat sinks, but have failed to test devices using structured copper because of the high ultrasonic attenuation. An assembled device having a silicon wafer bonded both above and below to structured copper disks cannot, until now, be tested with high frequency ultrasound, X-ray, infrared, or electrical performance tests. The structured copper is pliable and formed of parallel, equal length, closely packed strands of copper, and accommodates to the difference in expansion between the semiconductor and fluid cooled metal heat sink.

SUMMARY OF THE INVENTION

Unbonded areas between the metal layers on a semiconductor wafer and a structured coppper heat sink member are detected by scanning the assembled device in a liquid bath with pulses of ultrasound that are focused to a small spot at the ends of the copper strands. The acoustic energy is transmitted along the strand, similar to the transmission of light by an optical fiber, and is highly attenuated in the lateral direction. Very little beam spreading occurs in the semiconductor layers. The transmitted ultrasound pulse, assuming a good bond, is detected by a receiving transducer and a received signal is generated. When there is a void between the copper strands and semiconductor wafer, the sound does not penetrate as well to the other surface of the assembled device and there is a low amplitude or no received signal. The unbonded areas may be mapped with high lateral resolution and the unbond size determined. This nondestructive test is applied to devices such as large photovoltaic cells with structured copper bonded to one surface of the semiconductor wafer, and power thyristors which have structured copper bonded to both surfaces of the wafer.

The assembled device is scanned by a doubly focused system having focused transmitting and receiving transducers on a common axis and the received signal is displayed on an oscilloscope. Alternatively a scanning acoustic microscope and a gray scale recorder are employed to produce the bond interface image. The transmitting transducer is focused onto a bundle of copper strands and the receiving transducer is unfocused. There is a defective bond if the void areas exceed, say, 10-15 percent of the total bond area.

DESCRIPTION OF THE PREFERRED EMBODIMENTS

Figure 1:
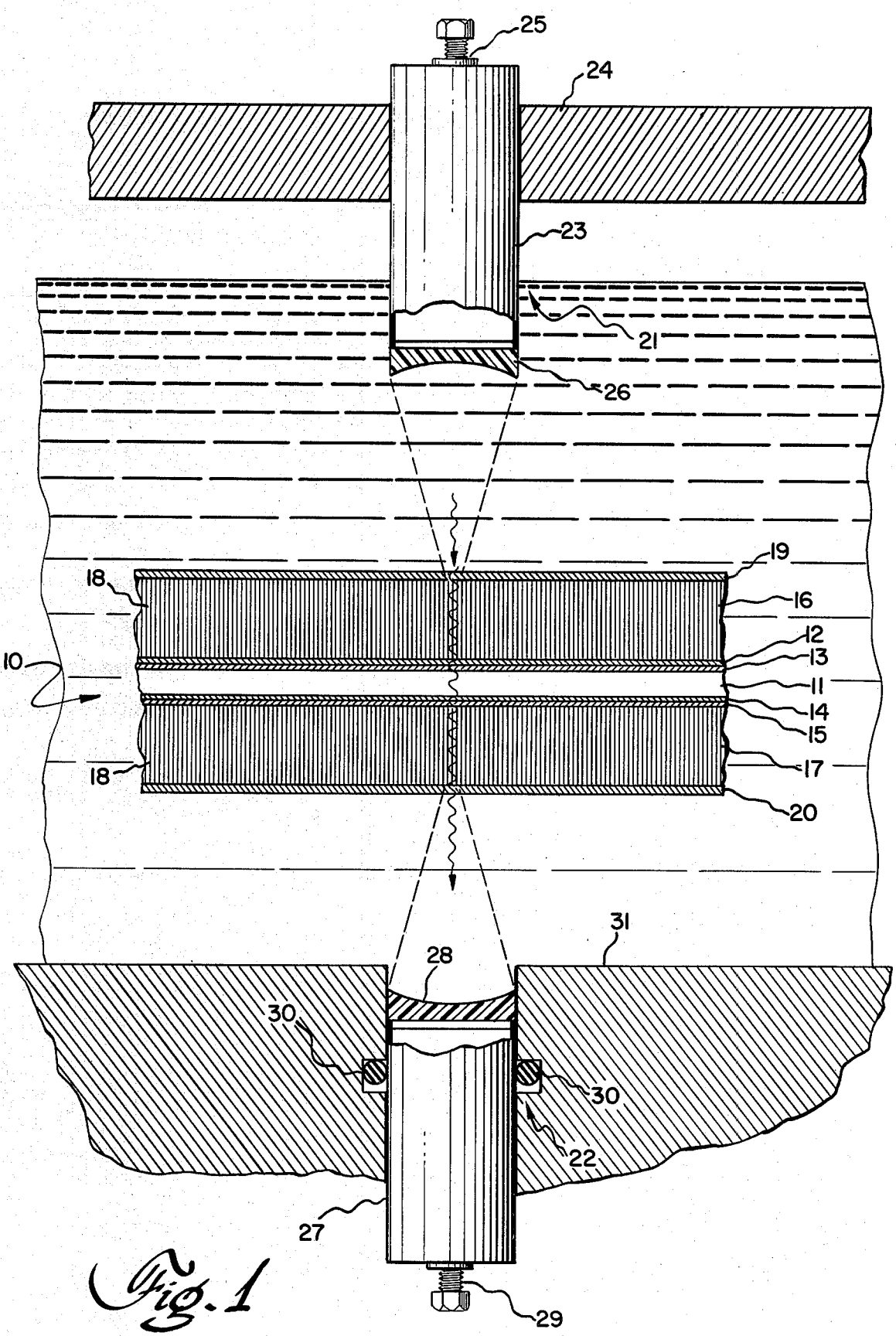
FIG. 1 illustrates focused transmitting and receiving transducers and the pulse transmission testing of a semiconductor device with structured copper on both sides.

The low thermal expansion of the silicon wafer in comparison to the metals used for liquid and air cooled heat sinks, leads to substantial thermal induced stress after both materials have cooled down from the bonding temperatures and during thermal cycling in the course of normal operation. To eliminate these thermal stresses, structured copper layers have been introduced to provide mechanical compliance between the low expansion silicon and the relatively high expansion copper heat sinks. In FIG. 1, assembled semiconductor device 10 has a silicon wafer 11 which is a multilayer power device such as a thyristor, transistor, or diode, and one such device has deposited metal layers 12-15 on the top and bottom surfaces of the wafers. The inner metallic layers 13 and 14 are made of titanium, chromium, or nickel, and the outer layers 12 and 15 are highly electrically conductive metals such as copper, gold, or silver. Structured copper strain relieving heat sink disks 16 and 17 are bonded above and below the silicon device, and are formed of substantially parallel strands of copper 18 at a density near 90 percent. The structured copper disk exhibits substantial structural integrity while still allowing individual movement of the separate strands of copper in the plane of the disk so as to provide substantial stress relieving capability together with high thermal conductivity. It provides a good electrical connection to the wafer while also providing a good thermal path away from the device for the generated heat. The ends of copper strands 18 are thermo-compression diffusion bonded or soldered directly to metal layers 12 and 15, and the integrity of these bonds is being tested, i.e., the copper-to-copper bond, copper-to-gold bond, or copper-to-silver bond. The outer ends of copper strands 18 are usually diffusion bonded to copper foil disks 19 and 20, although this is not essential. The copper foil disks are in turn diffusion bonded above and below assembled device 10 to fluid cooled copper heat sinks to which two power leads are attached and conduct current to and away from the device.

A more detailed description of assembled semiconductor device 10 and other configurations of the fluid cooled, structured copper power device are given in copending application Ser. No. 958,100, filed on Nov. 6, 1978 by H. H. Glascock, II, D. E. Houston, M. H. McLaughlin, and H. F. Webster. In the thermocompression diffusion bonding process, the foil 19 or 20 is joined to and diffused into a common end of the bundle of copper strands 18; this process and the structured copper member are described in U.S. Pat. No. 4,252,263 granted to D. E. Houston. Both are assigned to the same assignee as this invention. A typical diffusion bond is accomplished at a temperature of 300° C. for one-half hour to one hour at a pressure of 7000 lbs/in$^2$. Voids and unbonded areas at the bond interface occur because of improper contact, contaminated surface area, wires torn loose, etc. A fatigue-resistant solder, such $92\frac{1}{2}$ percent lead, $2\frac{1}{2}$ percent silver, and 5 percent tin, is used to make a solder bond. These bonds can have bubbles and are defective if they have an excessive amount of voids and unbonded areas.

Sound focused onto the ends of the copper strands 18 is transmitted along the strands in the longitudinal direction but is highly attenuated in the lateral direction. Measurements of the sonic transparency of structured copper showed progressively less energy passed above 5 MHz in the direction of the fibers and almost no energy could be transmitted perpendicular to the fibers above 1 MHz. At 5 MHz, the attenuation along the fiber direction was almost 40 dB shown from the attenuation perpendicular to the fiber. Therefore, sound focused on the strand ends is transmitted down the strands, through the metal layers to the silicon wafer 11 and then away from the silicon by the lower structured copper plate. Very little beam spreading occurs except in the silicon wafer. In the structured copper member, the acoustic isolation between the strands which is demonstrated by the 40 dB increase in attenuation for the perpendicular propagation direction prevents beam spreading. The sound does not penetrate as well through to the other side of assembled semiconductor device 10 when there is a faulty bond between structured copper disk 16 or 17 and the semiconductor wafer.

A doubly focused ultrasonic pulse transmission test is performed with the apparatus in FIG. 1. Focused transmitting transducer 21 and focused receiving transducer 22 are on a common axis and the test is conducted under water. Transmitting transducer 23 contains a flat piezoelectric element, and is mounted on a support 24 and has an electrical terminal 25. The ultrasound pulse is focused by plastic lens 26 onto the ends of a small bundle of copper strands 18; there is some refraction in copper foil 19. The focal spot has a diameter of about 30 mils, and even higher lateral resolution than this is possible. The copper fiber diameter is on the order of 5–10 mils and the thickness of the structured copper disk is typically 100 mils. The transmitted pulse is collimated by the strands of copper, passes through good bonds and the metal layers 12–15, and through silicon wafer 11 with little beam spreading, and then is collimated by the opposing copper strands in the second structured copper disk 17.

Receiving transducer 22 is comprised of a transducer assembly 27, converging lens 28, and a terminal 29, and is mounted with an "O" ring seal 30 in a hole in a bottom support structure 31. The small focal spot of the focused transducer is placed approximately at the bottom surface of assembled semiconductor device 10, at the ends of the opposing bundle of copper strands 18. There is a received pulse when there is a good bond of the structured copper to semiconductor wafer metal layers 12 and 15; when the pulse ceases or there is a significantly reduced amplitude, there is a void and the bond is defective.

Figure 2:
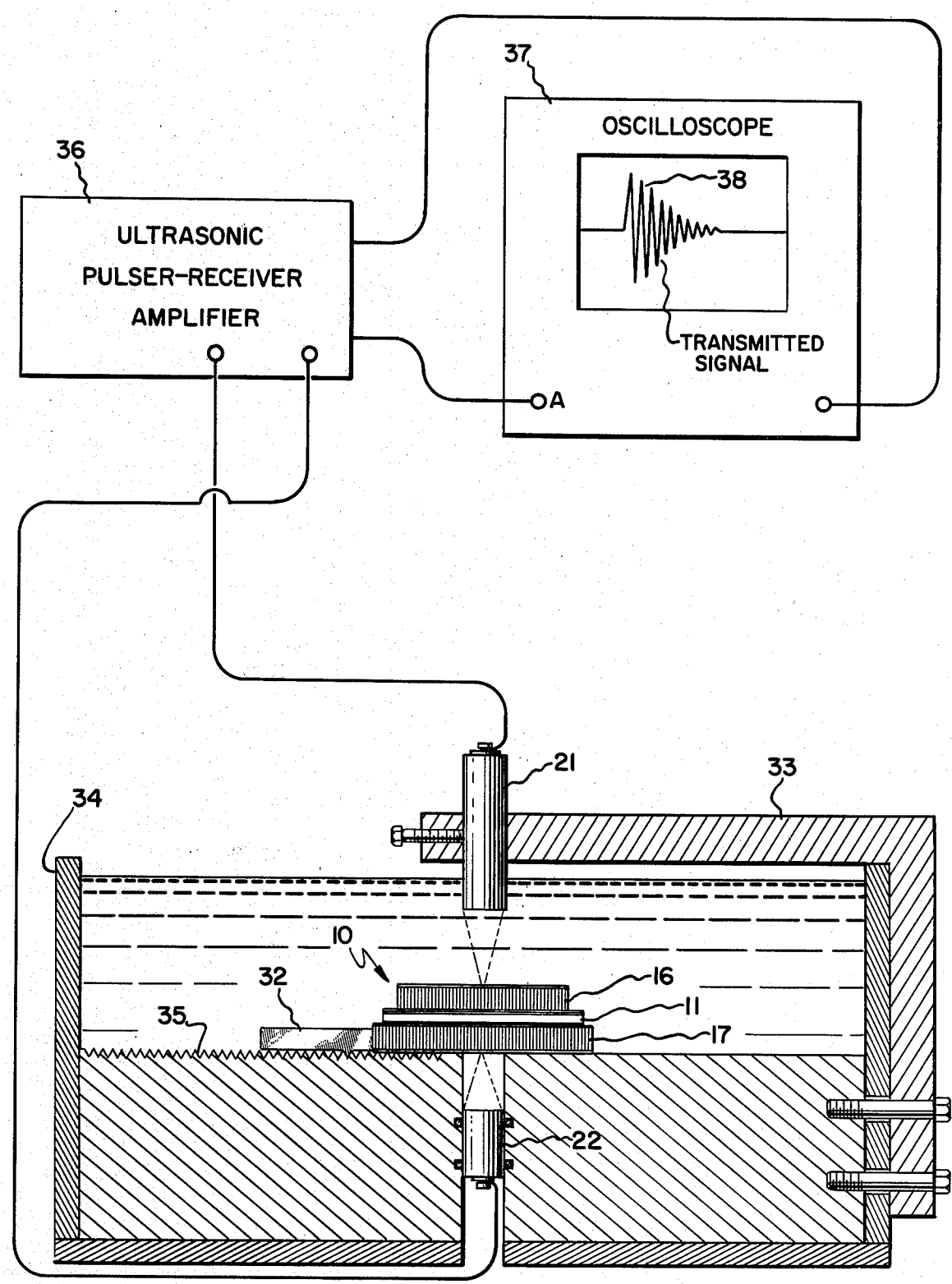
FIG. 2 shows apparatus having a doubly focused system which detects and displays unbonded areas in the bond layers.

The equipment in FIG. 2 has manual scan capability and performs a doubly focused ultrasound pulse transmission test on assembled semiconductor device 10 utilizing the small focal spot size available in the water coupling medium to produce a high lateral resolution for displaying and mapping the unbonded areas. It is constructed to rigidly support and align one-quarter inch diameter focused transmitting and receiving tranducers 21 and 22 on a common acoustic axis. Test piece 10 is fastened to a pallet 32 that is moved between the transmission of ultrasound pulses to make a raster scan of the semiconductor device. Transmitting transducer 21 is fixed in place and supported on an arm 33 that is fastened to the side of a receptacle 34 filled with water. Triangular grooves 35 on the support member inside of the tank receive a tooth on pallet 32. Transmitting and receiving transducers 21 and 22 are connected to an ultrasound pulser-receiver amplifier 36, and the received signal is fed to the vertical amplifier input of an oscilloscope 37. The other connection is to the time base input.

Excitation voltage produced by the pulser is applied to transmitting transducer 21 which generates a focused pulse of ultrasound. A high amplitude received signal 38 observed on the oscilloscope screen indicates a satisfactory bond of the structured copper disks 16 and 17 to semiconductor wafer 11. No received signal indicates a void or unbonded area which is larger than the acoustic beam. A small void whose size is less than the acoustic beam cross section produces a big drop in the amplitude of the received signal 38. As the test piece is scanned relative to the fixed acoustic beam, the amplitude of received signal 38 is observed and a plot of position versus amplitude is made. The detection of 10–15 percent voids (or any other given percentage) is cause for rejection of the semiconductor device.

Figures 3, 4:
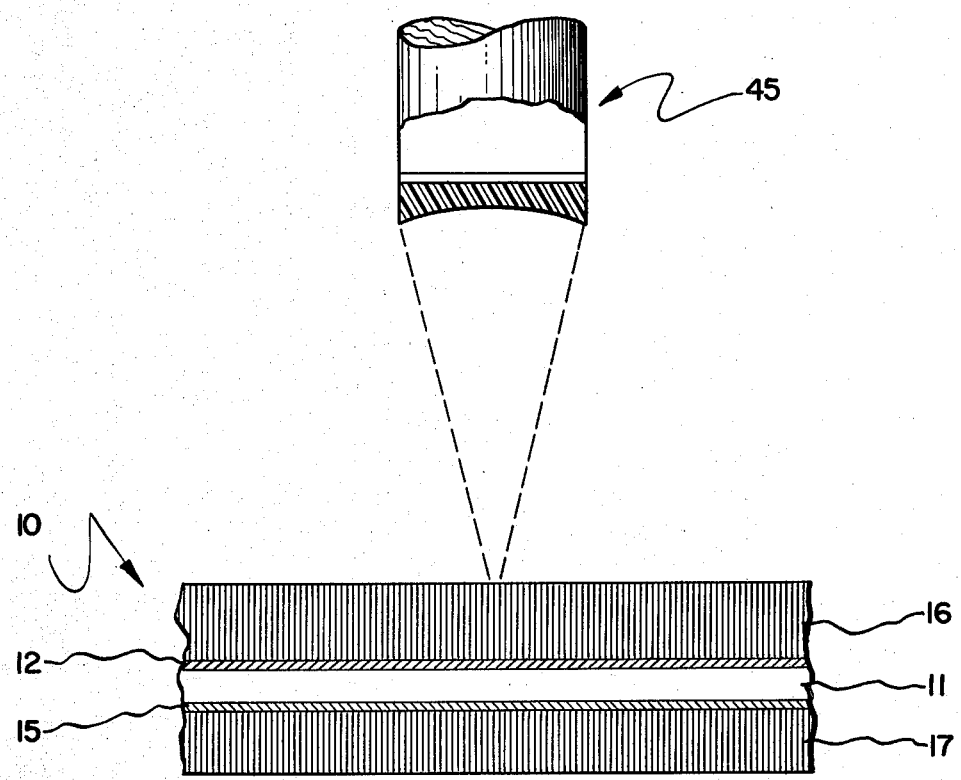
FIG. 3 is a side view of a solar cell sealed to structured copper.
FIG. 4 is a side view of a focused transmitting transducer and an unfocused receiving transducer for the ultrasonic transmission test.

The same procedure is used to test the bond integrity of a photovoltaic cell 40, FIG. 3, which is sealed to a structured copper strain relieving heat sink member 41. The upper free ends of copper wires 42 are soldered or may be thermo-compression diffusion bonded directly to base metallization 43, which is palladium-silver or chrome-nickel-copper. Copper foil disk 44 is diffusion bonded to the other ends of the copper wires and is in turn sealed to the copper heat sink. This structured copper semiconductor device is the subject of the present inventors' copending application Ser. No. 213,259 filed on Dec. 5, 1980. The fluid cooled silicon photovoltaic cell is exposed to highly concentrated sunlight and held at a relatively low temperature so as to maintain the efficiency of solar power to electrical power conversion.

The test equipment preferably includes a scanning acoustic microscope and gray scale recorder for automatically mapping the unbonded areas. The acoustic system in FIG. 4 has a focused transmitting transducer 45 and, on a common axis, an unfocused receiving transducer 46. The advantage of this is that the alignment is nowhere near as critical as in the doubly focused system. The focal spot of transmitting transducer 45 is placed approximately at the upper ends of the copper wires in structured copper disk 16, and the pulses of ultrasound transmitted through assembled device 10 emerge as spherical waves. Receiving transducer 46 has a flat transducer element 47 and is less sensitive than the focused transducer. Alternatively, the transmitter is unfocused and the receiver is focused. Small one-quarter inch diameter transducers and possibly one-eighth inch diameter units are used.

Figure 5:
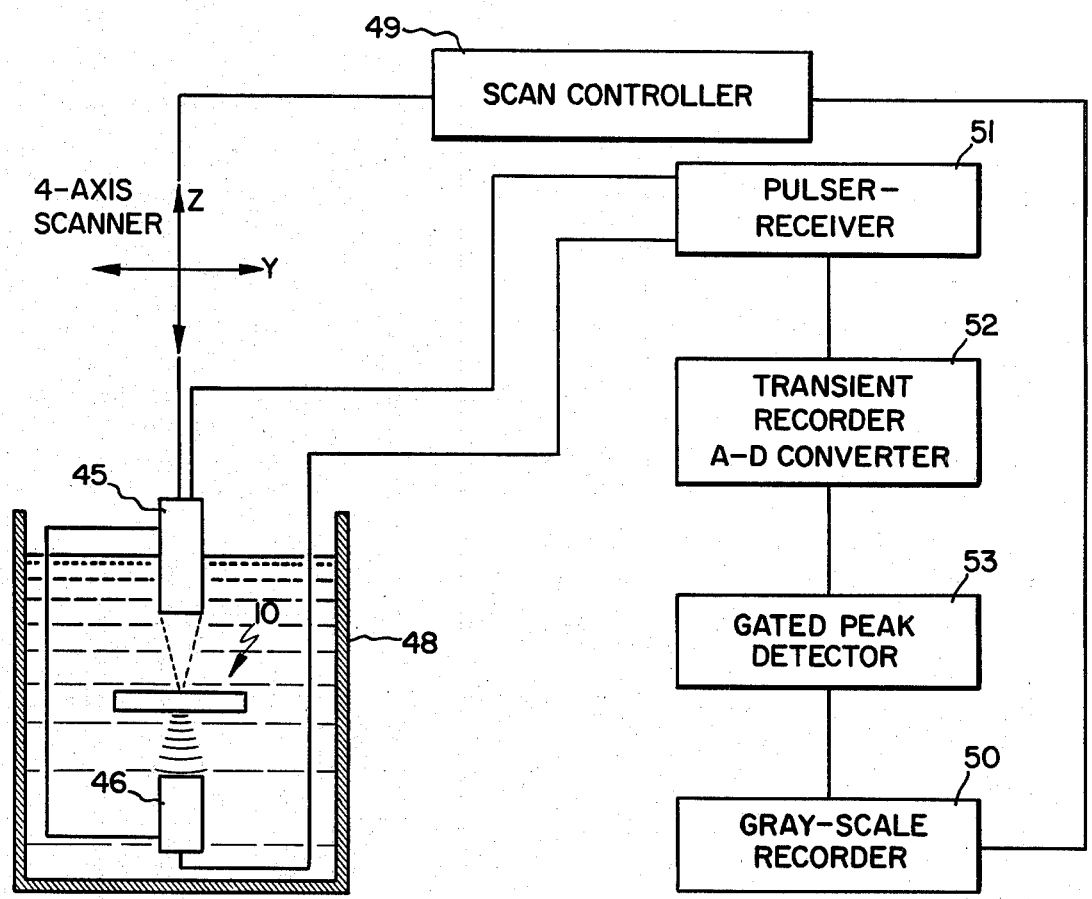
FIG. 5 is a diagram of test equipment with a scanning acoustic microscope.

The scanning acoustic microscope depicted schematically in FIG. 5 is built from purchased components. In the water bath container 48, test piece 10 is stationary and aligned transmitting and receiving transducers 45 and 46 are indexed by a four-axis scanner. The latter is actuated by a scan controller 49 and its current position is relayed to a gray scale recorder 50. Pulser-receiver 51 excites focused transmitting transducer 45 and the pulse of ultrasound is detected by unfocused receiving transducer 46 and converted to an electrical signal which is amplified by the receiver. The received signals are fed to a transient recorder 52 and hence converted to digital data by the analog-to-digital converter. The peak voltage of the received signal is determined by gated peak detector 53 and this information is presented to gray scale recorder 50 which has a dynamic range of several steps of gray.

Figure 6:
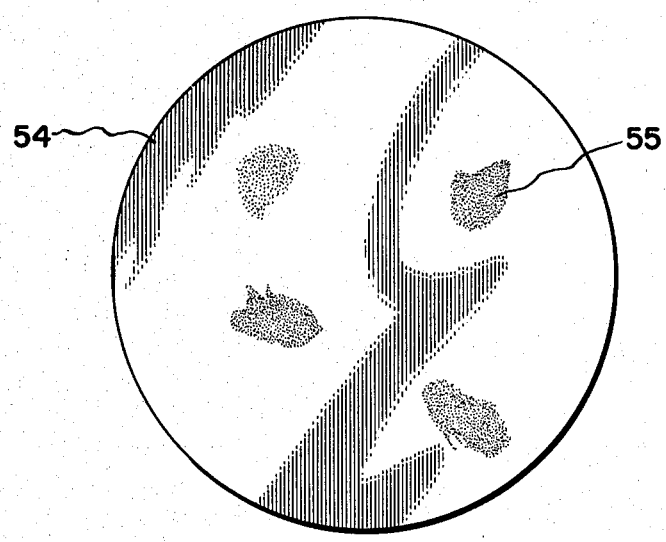
FIG. 6 shows a bond interface image produced by the gray scale recorder in FIG. 5.

The voids and unbonded areas are mapped by the recorder and a typical bond interface image 54 is shown in FIG. 6. Logic is provided so that high amplitude received signals representing good bonds are printed out as white and low amplitude received signals and the absence of a received signal, representing voids and unbonded areas, are printed out in darker shades of gray and black. If the sum of the areas of the voids 55 is greater than say 15 percent of the total bond area, the semiconductor device may fail and the part is rejected. The automatic test apparatus is capable of evaluating the bonds in a circular device three inches in diameter in less than 60 seconds. The four-axis scanner and scan controller are, for instance, Anorad, Inc. Model 601 and the gray scale recorder is the Raytheon Oceanographic Systems, Inc. Universal Graphic Recorder. The transducer is a Panametric 5 MHz device.

The method makes use of the physical properties of structured copper, specifically the directional attenuation to realize high lateral resolution. An equivalent resolution using the pulse echo test, rather than the pulse transmission test, would require the silicon layer exposed to the incident signal and a test frequency equal to at least four times the 5 MHz frequency used, in order to separate the signals in the silicon layer. The pulse transmission test can be applied to an assembled semiconductor device consisting of a silicon wafer bonded both above and below by structured copper layers, and an assembled device having structured copper bonded to one side of the silicon wafer.

While the invention has been particularly shown and described with reference to preferred embodiments thereof, it will be understood by those skilled in the art that various changes in form and details may be made therein without departing from the spirit and scope of the invention.

The invention claimed is:

1. The method of testing an assembled semiconductor device for unbonded areas in the bond between a metal layer on a semiconductor wafer and a structured copper heat sink member which has substantially parallel closely packed strands of copper, comprising the steps of:
   scanning said assembled device with pulses of ultrasound which are incident on one surface thereof and are transmitted along said copper strands and highly attenuated in the lateral direction, and pass through said bond and metal layer and said semiconductor wafer without significant lateral spreading;
   detecting the ultrasound pulses that are transmitted to the other surface of said assembled device and producing received electrical signals; and
   processing and displaying said received signals such that a high amplitude signal designates a good bond and a low amplitude or no signal designates voids and unbonded areas in the bond of said structured copper member to the semiconductor wafer metal layer.

2. The method of claim 1 wherein said pulses of ultrasound have a frequency of about 5 MHz and the bond testing is performed in a water bath.

3. The method of claim 1 wherein said pulses of ultrasound are focused to a small spot and are incident on the ends of a bundle of said copper strands.

4. The method of claim 1 wherein said pulses of ultrasound are generated by a focused transmitting transducer and the transmitted pulses are detected by an unfocused receiving transducer.

5. The method of testing an assembled semiconductor device for voids and unbonded areas in the bonds above and below metal layers on a semiconductor wafer to structured copper heat sink members which have substantially parallel closely packed strands of copper, comprising the steps of:
   scanning said assembled device in a water bath with pulses of ultrasound which are focused to a small spot at the end of a bundle of copper strands of one structured copper member and are transmitted along said copper strands and highly attenuated in the lateral direction, and pass through said bonds and metal layers and said semiconductor wafer without significant lateral spreading;
   detecting the ultrasound pulses that are transmitted through said assembled device and generating received electrical signals; and
   producing a bond interface image in which high amplitude received signals designate a good bond and low amplitude or no received signals designate a defective bond.

6. The method of claim 5 wherein said received signals are peak detected and said bond interface image has shades of gray.

7. The method of claim 5 wherein said assembled device is scanned with a scanning aocustic microscope having a focused transmitting transducer and an unfocused receiving transducer on a common axis.

8. The method of claim 7 wherein the frequency of said pulses of ultrasound is about 5 MHz.

9. The method of claim 8 wherein said bond interface image has shades of gray depending on the received signal amplitude.

10. The method of testing an assembled semiconductor device for voids and unbonds in the bond of a metal layer on a semiconductor wafer to a structured copper heat sink member which has substantially parallel closely packed strands of copper, comprising the steps of:
   scanning said assembled device relative to a doubly focused acoustic system having focused transmitting and receiving transducers on a common axis;
   exciting said transmitting transducer to generate pulses of ultrasound that are focused to a small spot approximately at one surface of said assembled device and are transmitted along said strands of copper and highly attenuated in the lateral direction, and pass through said bond and metal layer and said semiconductor layer without significant lateral spreading;

the transmitted ultrasound pulses being focused onto said receiving transducer which produces received electrical signals; and processing and mapping said received signals to produce a bond interface image in which high amplitude received signals designate a good bond and low amplitude or no received signals designate voids and unbonds.

* * * * *